(12) United States Patent
Hadida et al.

(10) Patent No.: US 12,057,227 B2
(45) Date of Patent: Aug. 6, 2024

(54) TELEHEALTH CONTROL SYSTEM AND METHOD FOR ENGAGING PROVIDERS

(71) Applicant: MDLIVE, Inc., Miramar, FL (US)

(72) Inventors: Axel Hadida, Plantation, FL (US); Ackeem Rose, Margate, FL (US)

(73) Assignee: MDLive, Inc., Miramar, FL (US)

( * ) Notice: Subject to any disclaimer, the term of this patent is extended or adjusted under 35 U.S.C. 154(b) by 266 days.

(21) Appl. No.: 17/743,818

(22) Filed: May 13, 2022

(65) Prior Publication Data

US 2022/0367045 A1 Nov. 17, 2022

Related U.S. Application Data

(60) Provisional application No. 63/188,882, filed on May 14, 2021.

(51) Int. Cl.
| | |
|---|---|
| *G16H 40/67* | (2018.01) |
| *G06N 3/02* | (2006.01) |
| *G16H 40/20* | (2018.01) |
| *G16H 80/00* | (2018.01) |
| *H04W 4/14* | (2009.01) |

(52) U.S. Cl.
CPC ............. *G16H 40/67* (2018.01); *G06N 3/02* (2013.01); *G16H 40/20* (2018.01); *G16H 80/00* (2018.01); *H04W 4/14* (2013.01)

(58) Field of Classification Search
CPC ........ G16H 40/67; G16H 40/20; G16H 80/00; G06N 3/02; G06N 3/044; G06N 3/0464; H04W 4/14

See application file for complete search history.

(56) References Cited

U.S. PATENT DOCUMENTS

| | | |
|---|---|---|
| 10,796,795 B1 | 10/2020 | Bullington |
| 2004/0181428 A1 | 9/2004 | Fotsch |
| 2011/0106557 A1 | 5/2011 | Gazula |

(Continued)

FOREIGN PATENT DOCUMENTS

KR 20180003016 A * 1/2018

OTHER PUBLICATIONS

Baek, Susan. Update: telemedicine. West Virginia Medical Journal 111.6: 38(3). West Virginia State Medical Association. (Nov. 2015-Dec. 2015) (Year: 2015).*

(Continued)

*Primary Examiner* — Linh Giang Le
(74) *Attorney, Agent, or Firm* — The Small Patent Law Group (57) ABSTRACT

A system and method for engaging healthcare providers with patients in virtual encounters send a notification message to a computing device of one or more healthcare providers via a first communication channel that is outside of a telehealth system software application and a telehealth system website. A reply message is received from the computing device via the first communication channel. The reply message indicates acceptance of at least one of the virtual encounters by the one or more of the healthcare providers. The system and method also establish the at least one of the virtual encounters between the one or more of the healthcare providers and the one or more of the patients via a second communication channel that is different from the first communication channel.

20 Claims, 8 Drawing Sheets

(56) References Cited

U.S. PATENT DOCUMENTS

| | | |
|---|---|---|
| 2014/0316810 A1 | 10/2014 | Oliver |
| 2014/0365240 A1 | 12/2014 | Canton |
| 2016/0203270 A1 | 7/2016 | Sabala |
| 2017/0011179 A1 | 1/2017 | Arshad |
| 2017/0011192 A1 | 1/2017 | Arshad |
| 2017/0011193 A1 | 1/2017 | Arshad |
| 2017/0011194 A1 | 1/2017 | Arshad |
| 2017/0011196 A1 | 1/2017 | Arshad |
| 2017/0011200 A1 | 1/2017 | Arshad |
| 2021/0057111 A1* | 2/2021 | Barkol .................. H04L 51/046 |

OTHER PUBLICATIONS

Consult QD, For Arrhythmia Patients, Virtual Visits Hold Plenty of Virtues. Dec. 15, 2016 Heart, Vascular and Thoracic.

Jackson, Coronavirus offers opportunity for physicians to try telemedicine; https://www.medicaleconomics.com/view/coronavirus-offers-opportunity-physicians-try-telemedicine; accessed as early as May 9, 2021.

* cited by examiner

TELEHEALTH CONTROL SYSTEM AND METHOD FOR ENGAGING PROVIDERS

CROSS-REFERENCE TO RELATED APPLICATIONS

This application claims priority to U.S. Provisional Application No. 63/188,882 (filed 14 May 2021), the entire disclosure of which is incorporated herein by reference.

BACKGROUND

Many different types of services can be provided via distributed or long-distance systems. For example, telehealth systems can provide health-related services and information via electronic information and telecommunication technologies. These systems can allow for long-distance provider and customer interaction via video conferencing and/or telephone calls. With respect to telehealth systems, healthcare providers may be able to be reached for consultations, medical appointments, etc., for a variety of medical issues.

With respect to telehealth systems, patients may seek an appointment with a healthcare provider via a remote encounter (e.g., a videoconference or teleconference). The patients may be placed into a virtual waiting room until a suitable and available healthcare provider is found. Once the suitable and available healthcare provider is found, the remote encounter may be established, and the patients may remotely interact with the providers to receive medical care, advice, and the like.

BRIEF DESCRIPTION

In one example of the subject matter described herein, a method for engaging healthcare providers with patients in virtual encounters is provided. The method includes determining that one or more of the patients are waiting for the virtual encounters with the healthcare providers via a telehealth system software application or via a telehealth system website. The application can be operating on computing devices of the healthcare providers. The telehealth system website can be accessible via the computing devices of the healthcare providers. The method also can include sending a notification message to the computing device of one or more of the healthcare providers via a first communication channel that is outside of the telehealth system software application and the telehealth system website, receiving a reply message from the computing device of the one or more of the healthcare providers via the first communication channel. The reply message indicates acceptance of at least one of the virtual encounters by the one or more of the healthcare providers. The method also includes establishing the at least one of the virtual encounters between the one or more of the healthcare providers and the one or more of the patients via a second communication channel that is different from the first communication channel.

In another example, a telehealth control system for engaging healthcare providers with patients in virtual encounters is provided. The telehealth control system includes one or more processors configured to determine that one or more of the patients are waiting for the virtual encounters with the healthcare providers via a telehealth system software application operating on computing devices of the healthcare providers or via a telehealth system website accessible via the computing devices of the healthcare providers. The one or more processors are configured to send a notification message to the computing device of one or more of the healthcare providers via a first communication channel that is outside of the telehealth system software application and the telehealth system website. The one or more processors are configured to receive a reply message from the computing device of the one or more of the healthcare providers via the first communication channel. The reply message indicates acceptance of at least one of the virtual encounters by the one or more of the healthcare providers. The one or more processors are configured to establish the at least one of the virtual encounters between the one or more of the healthcare providers and the one or more of the patients via a second communication channel that is different from the first communication channel.

In another example, a method for engaging service providers with consumers in virtual encounters is provided. The method includes determining that one or more of the consumers are waiting for the virtual encounters with the service providers via a software application operating on computing devices of the service providers or via a system website accessible via the computing devices of the service providers, sending a notification message to the computing device of one or more of the service providers via a first communication channel that is outside of the software application and the system website, and receiving a reply message from the computing device of the one or more of the service providers via the first communication channel. The reply message indicates acceptance of at least one of the virtual encounters by the one or more of the service providers. The method also includes establishing the at least one of the virtual encounters between the one or more of the service providers and the one or more of the consumers via a second communication channel that is different from the first communication channel.

BRIEF DESCRIPTION OF THE DRAWINGS

In the drawings, reference numbers may be reused to identify similar and/or identical elements.

DETAILED DESCRIPTION

Some telehealth systems may suffer from inefficiencies in initiating the encounters between the providers and patients. For example, some telehealth systems may rely on providers being located at desktop or laptop computer stations to receive invitations to remote encounters with patients and/or to be notified of patients waiting in virtual waiting rooms for the remote encounters. With ever-increasing mobile healthcare workforces, however, providers may be away from such stations more often. Additionally, requests from patients for remote encounters may occur at times of the day (e.g., the middle of the night) and/or on dates (e.g., holidays or weekends) when appropriate providers are not readily available to receive notifications of the requested remote encounters. Accordingly, this disclosure addresses a need to reduce or eliminate the inefficiencies that exist with at least some of the telehealth systems for connecting patients with providers.

Example systems and methods for engaging providers of services via a virtual encounter with consumers of the services that are waiting in virtual waiting rooms are described herein. The providers may be healthcare providers while the consumers are patients in an embodiment for ease of illustration and explanation, although not all embodiments of the inventive subject matter are limited to healthcare services (as described below). The healthcare providers and patients may interact with each other via a videoconference or teleconference channel (e.g., using electronic communication devices connected over a communication network or channel), while the systems and methods provide for a different, separate channel for contacting the healthcare providers, confirming the availability of the healthcare providers for interacting with the patients via the videoconference or teleconference channel, and/or initiating the encounter via the videoconference or teleconference channel. As an example, the different, separate channel may be communication packets, e.g., messages, sent to the provider(s) via short messaging service (SMS) text messages. Because the messages sent via the different, separate channel are received by the providers via handheld devices that are carried by or are otherwise with the providers nearly around-the-clock (e.g., mobile phones), the providers may receive the messages for initiating the encounters with patients more quickly and/or reliably than currently known techniques (e.g., sending messages via the same website or software applications that provide the videoconference or teleconference channel). This separate channel may be selected from among two or more different available channels. For example, the separate channel may be selected from one or more encrypted channels, one or more unencrypted channels, a text-only channel (e.g., an SMS channel), a video channel (e.g., a communication channel that allows persons to communicate using video), a sound only channel (e.g., a telephone communication channel or other channel that communicates sound but not video), or the like. The type of message sent via this separate channel may be selected from among different types of messages. For example, the message sent via the separate channel may be a text-only message (e.g., a signal containing text but no images, video, or sound), a multimedia message (e.g., a signal containing two or more of an image, a video, and/or a sound), a sound-only message (e.g., a telephone call), a private and/or encrypted message or signal, a public and/or unencrypted message or signal, etc. The messages can be a combination of two or more of these types of messages separate from the main channel.

Figure 1:
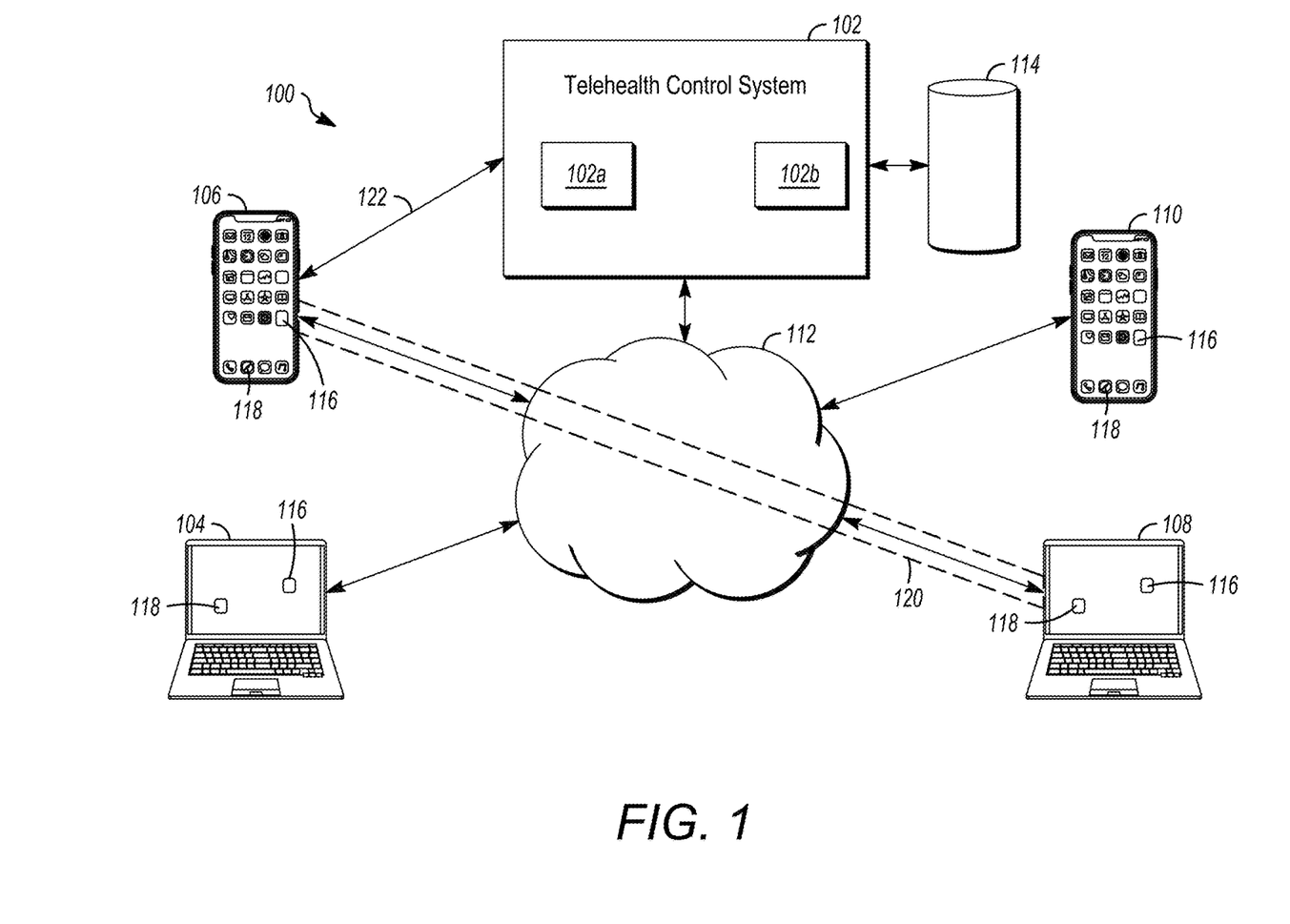
FIG. 1 illustrates one example of a telehealth system.

FIG. 1 illustrates one example of a telehealth system 100. The telehealth system 100 may be used to establish and conduct remote encounters between healthcare providers and patients. A remote encounter may include an interaction (e.g., meeting, medical appointment, medical consultation, etc.) between a healthcare provider and a patient via video conference or teleconference while the healthcare provider and the patient are in different locations (e.g., different rooms, different buildings, different towns or cities, different zip codes, different states, or different countries). The healthcare provider can be a Doctor of Medicine, Doctor of Osteopathy, a podiatrist, a dentist, a chiropractor, a clinical psychologist, an optometrist, a nurse practitioner, a nurse-midwife, or a clinical social worker. While the examples described herein relate to the system 100 being used to establish remote encounters between healthcare providers and patients, not all embodiments of the inventive subject matter are limited to telehealth systems. For example, the system 100 optionally can be used to establish and conduct remote encounters between real estate agents and clients, between attorneys and clients, courts and parties, teachers and students, governmental meetings, voter and election systems, or any other service provider and customer who are connected via an electronic communication system.

The system 100 includes a telehealth control system 102 that represents hardware circuitry having and/or connected with one or more processors (e.g., microprocessors, field programmable gate arrays, integrated circuits, etc.) that perform the operations described in connect with the control system 102. The control system 102 communicates (wirelessly and/or via wired connections) with provider computing devices 104, 106 and consumer or patient computing devices 108, 110. The computing devices 104, 108 can represent laptop computers, desktop computers, tablet computers, or the like, and the computing devices 106, 110 can represent mobile phones. Each of these devices may be operating as dedicated machines when the instructions for performing the methods described herein are loaded from a memory to be executed on processing circuitry.

The control system 102 can manage a virtual encounter between the providers and patients by establishing a communication channel between a computing device 104 or 106 of the provider(s) and a computing device 108 or 110 of the patient, e.g., though the first communication subsystem 102A. The control system 102 can assign a unique identifying code to the provider device 104, 106 and the patient device 108, 110. The unique code can be a unique short code for each device, which allows the control system 102 to securely and uniquely establish an appropriate connection between a patient and a provider. This communication channel can be a videoconference or a teleconference that extends through one or more computer networks 112, such as the Internet, one or more intranets, one or more local area networks, or the like. The computing devices 104, 106, 108, 110 may have software applications 116 installed or otherwise running thereon to establish a secure connection between (a) the provider computing device 104 or 106 and (b) the patient computing device 108 or 110. These software applications 116 can be commercial or proprietary applications 116 used by a company or government to manage the remote encounters between providers and patients. The applications 116 can be installed in internal computer memories of the computing devices 104, 106, 108, 110 or may be accessed via web pages 118. One example of such a software application 116 or service is MDLIVE healthcare services that provides remote healthcare services e.g., via telephone, video, email, mobile devices or a global computer network.

The secure connection can extend through the network(s) 112 to ensure confidentiality of the information communicated between the provider and the patient. For example, the videoconference or teleconference channel can extend through one or more digital subscriber lines, cable modems, network fibers, wireless networks, satellite networks, broadband over powerline connections, etc., using the transmission control protocol over Internet protocol, or another protocol.

A patient can submit a request for a virtual encounter to the control system 102 (and specifically, to the first channel control subsystem 102A) using the software application 116 installed on or accessible on a website 118 via a patient computing device 108 or 110. In FIG. 1, reference number 118 can represent this website that is accessed by an Internet browser. This request can identify the patient, one or more health consultation needs of the patient, and other information. The health consultation needs may identify health issues or questions that the patient wishes to have resolved, answered, or otherwise addressed by a remote encounter with a provider. The control system 102 can use this information to identify one or more appropriate providers. For example, if the request identifies an issue related to the skin of the patient, then the control system 102 can determine that the appropriate provider is a dermatologist. if the request identifies an issue related to diabetes mellitus, then the control system 102 can determine that the appropriate provider is an endocrinologist, and so on. The control subsystem 102A may only send notifications to providers for the virtual encounters where the providers have education, expertise, training, and/or certification to provide service to treat the identified issue. The control subsystem 102A may controls the data being provided to the provider device to secure any patient identifying data and any patient health data.

The control system 102 can include or have access to a tangible and non-transitory computer readable medium, such as a database within a computer memory 114, which stores different specialties of the providers, contact information (e.g., phone numbers) of the providers, and so on. The control system 102 can include processing circuitry that is loaded with instructions from a memory to be a dedicated machine to perform tasks as described herein. The control system 102 can refer to information stored in the memory 114 to determine appropriate providers with which the videoconference or teleconference with the patient can be provided (based on information included in the request submitted by the patient).

Several patients may seek virtual appointments with the same type of physician (e.g., physicians with the same medical specialty) at the same time. The control system 102 may place these patients in a queue, or virtual waiting room. Providers can then send a message to the control system 102 (using the provider computing devices 104, 106) to accept a patient for a virtual encounter, e.g., through a first communication channel or through a secondary communication channel. The control system 102 can then establish a connection between the provider computing device 104 or 106 and the patient computing device 108 or 110 via the network(s) 112, such as a teleconference or videoconference, for the remote encounter to occur.

Some telehealth systems may send messages to the software applications 116 running on or accessed by the provider computing devices (e.g., via webpages) to inform the providers of one or more patients who are waiting for a virtual encounter with a provider. For example, these telehealth systems can send electronic signals or messages to the applications 116 provided by the telehealth systems that operate on the provider computing devices 104, 106 and/or that are running on webpages 118 accessed by the provider computing devices 104, 106 (websites 118 of the telehealth systems). Sending the messages in this way may only be effective to notify providers of the waiting patients during times that the providers have access to the provider computing devices 104, 106 with the applications 116 of the telehealth systems running on or being accessed by the provider computing devices 104, 106. If the providers are present at or are not using the provider computing devices 104, 106, or the applications 116 of the telehealth systems are not running on or being accessed by the provider computing devices 104, 106, then there may be a delay between when the message is sent and when the provider receives the message. With many patients waiting in the virtual waiting room, the delays in reaching providers can add up and result in significant waiting times for patients (e.g., at least three minutes of waiting time, at least fifteen minutes of waiting time, at least thirty minutes of waiting time, more than thirty minutes or the like). These delays can cause frustrated patients, and overall poor experiences for the providers and patients using the telehealth systems. Such delays may also result in increased consumption of computer resources.

In an embodiment of the inventive subject matter described herein, the control system 102, using a second channel control subsystem 102B, communicates a message with the provider computing device(s) 104, 106 via a different, second communication channel than the videoconference or teleconference channel (first or primary channel) to notify the provider(s) of the patient(s) waiting for a virtual appointment. The virtual appointment will occur in a communication channel separate from the second communication channel. In an example, the second channel control subsystem 102B is separate from the first channel control subsystem 102A, e.g., different hardware circuitry or different operating instructions. In an example, the second channel control subsystem 102B sets a lower level of security than the first channel control subsystem 102A. The provider computing devices 104, 106 can communicate with the patient computing devices 108, 110 to conduct the virtual appointment via a first channel 120 that extends between the applications 116 and/or websites 118 operating on or accessed by the devices 104, 106, 108, 110 via the network(s) 112. An example of the first channel 120 is shown in FIG. 1, although one or more other first channels 120 may be formed by the control system 102 using the applications 116 or websites 118.

But prior to establishing the first channel 120 over or through which the virtual appointment is conducted, the control system 102 (e.g., using the second channel control subsystem 102B) can send a message or signal to the provider computing device(s) 104, 106 via a second channel 122 that is different from the first channel 120. The second channel 122 can differ from the first channel 120 in that communication over or through the second channel 122 does not require or involve the first channel 120. The second channel 122 can represent communications that are not initiated, received, parsed, or examined by the applications 116 or websites 118. Additionally, the second communication channel 122 is not established to the patient devices. Using separate channels can avoid the delays associated with relying on the providers to use the applications 116 or websites 118 to receive the notifications that one or more patients are waiting for a virtual encounter in the virtual waiting room.

In an embodiment, communications via the second channel 122 can represent synchronous communications or communications sent over a synchronous communication channel, such as SMS text messages. The second channel 122 can be a packet communication channel that communicates short, text-based packets. In an example embodiment, the second channel packets of one hundred forty bytes, e.g., short messages. Such packets can be concatenated to reassemble longer messages. The short messages can be used to provide a complete reply from the provider device. The short message can also be easier for the telehealth control system 102 to interpret the return message from the provider device over the second communication channel 122. The use of messages may be more likely to be received by a mobile phone or other mobile device carried more often and/or for longer durations than the provider computing devices 104. For example, providers may have their cellular phones with them for longer periods of time during the day and/or night, and on more days, when compared to how often and long the providers are at a desktop computer or are using their cellular phones with the application 116 or website 118 operating. Sending the notification messages to the providers that patients are waiting in a virtual waiting room as SMS text messages can ensure that providers receive the notifications sooner than if the messages are sent via the first channel 120. This can result in reduced waiting times for patients (when compared with only using the first channel 120. For example, the average waiting time for patients in a virtual waiting room may be reduced by a factor of ten to fifteen (e.g., an average waiting time of thirty seconds to one minute).

Additionally, notifying the providers of the patients in the virtual waiting room over the second channel 122 and allowing the providers to select a patient from the virtual waiting room for a virtual encounter via the first channel 120 can allow for providers to be more easily reached in areas having lower demand for virtual encounters. For example, in some rural areas, the number or frequency of requests for virtual encounters may be less than that in urban areas. Consequently, most providers in the lower demand areas may rely more on messages sent via the second channel 122 to be reached for virtual encounters than on the application 116 or website 118 via the first channel 120.

In another embodiment, the first channel 120 (using the first channel subsystem 102A) can represent communications between the computing devices 104, 108 that are used by the patient and the provider to communicate with each other in the virtual encounter, while the second channel 122 can represent communications between one or more other computing devices that are not used by the patient and the provider to communicate with each other in the virtual encounter. For example, the virtual encounter may involve the patient and provider communicating via the first channel 120 using the provider computing device 104 and the patient computing device 108 or 110, while the communications involving the provider communication device 106 are the second channel 122.

In another embodiment, the first channel 120 can represent communications between the computing devices 104, 106 and 108, 110 using the application 116 or website 118 of the telehealth system 100, while the second channel 122 can represent communications between the computing devices 104, 106 and 108, 110 using another application or website. Optionally, the first channel 120 can represent communications between the computing devices 104, 106 and 108, 110 using the application 116 or website 118 of the telehealth system 100, while the second channel 122 can represent communications between the computing devices 104, 106 and 108, 110 that are in-app notifications of the application 116. Optionally, the first channel 120 can represent communications between the computing devices 104, 106 and 108, 110 using multimedia messaging service (MMS) messages while the second channel 122 can represent communications between the computing devices 104, 106 and 108, 110 that are in-app notifications of the application 116. Messages can be SMS text messages in an example embodiment.

In another embodiment, the first channel 120 extends through one or more nodes that are part of the publicly available Internet, while the second channel 122 extends through one or more cellular towers. The first channel 120 may not extend through any cellular towers while the second channel 122 may not extend through any nodes (e.g., routers) that are part of the publicly available Internet.

In an example embodiment, the notification message being sent over the second channel does not include any patient identifying information (PII) data, but does include general information (non-identifying information) about the patient and the result of the patient intake, which may assist in assigning the patient to the provider for virtual consultation using the systems and devices described herein. Likewise, in another example embodiment, the notification message does not include patient health information (PHI) data. In additional example embodiments, a patient device must be in electronic communication through the first channel before the system will send a communication message to the provider over the second communication channel.

Responsive to receiving a notification message via the second channel 122, the provider computing device 106 can send a reply message to the control system 102 via the same second channel 122. For example, the reply message can be another SMS text message sent to the control system 102. The reply message can accept the notification and cause the control system 102 to open or begin the virtual encounter or appointment between the provider and the patient via the first channel 120.

The second channel control subsystem 102B is separate from the first channel control subsystem 102A. The second channel control subsystem 102B can communicate messages to the provider devices. The data stored in the database 114 can be flagged as restricted data, e.g., either patient health data or patient identifying information. Other data stored in the database 114 is not restricted. The restricted data cannot be accessed or sent using the second channel control subsystem 102B. The restricted data can be accessed or sent using the first channel control subsystem 102A. The first channel control subsystem 102A can also record the first communication channel. The memory circuitry and data storage (e.g., including database 114) can store the communication over the first channel and the second channel. Both of these communications can be part of a single patient encounter record with the data being flagged as to the source of the data, whether the data contains patient identifying information (PII) data, patient health information (PHI) data, other restricted data and the like. These flags can be used to control access to the data.

Figure 2:
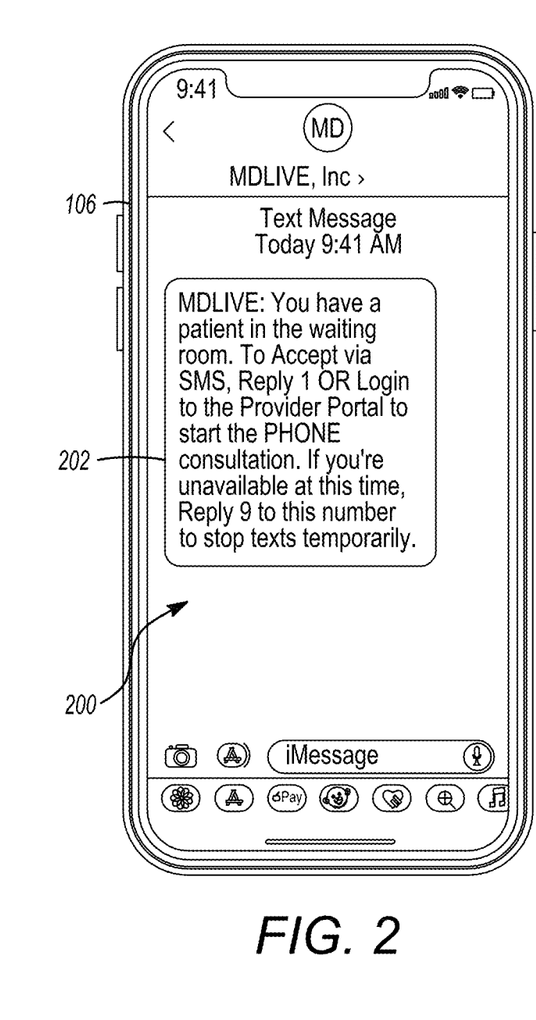
FIG. 2 illustrates an example of a graphical user interface (GUI) that can be displayed on a provider computing device shown in FIG. 1 to communicate notification and reply messages to a telehealth control system of the telehealth system.

FIGS. 2 through 8 illustrate different examples of GUIs 200, 300, 400, 500, 600, 700, 800 that can be displayed on the provider computing device 106 to communicate notification and reply messages to the control system 102 via the second channel 122. The GUI 200 shown in FIG. 2 represents a notification message 202 sent from the control system 102 to the provider computing device 106 via the second channel 122. This notification message 202 informs the provider that a single patient is waiting in the virtual waiting room for a teleconference and invites the provider to use his or her provider computing device 106 to send a reply message to accept the invitation to meet with the patient via the first channel 120. The notification message 202 also provides the provider with the option to send a reply message via the second channel 122 to decline the invitation to meet with the patient via the first channel 120 and to stop the control system 102 from sending additional notification messages via the second channel 122 for a temporary time period.

Figure 3:
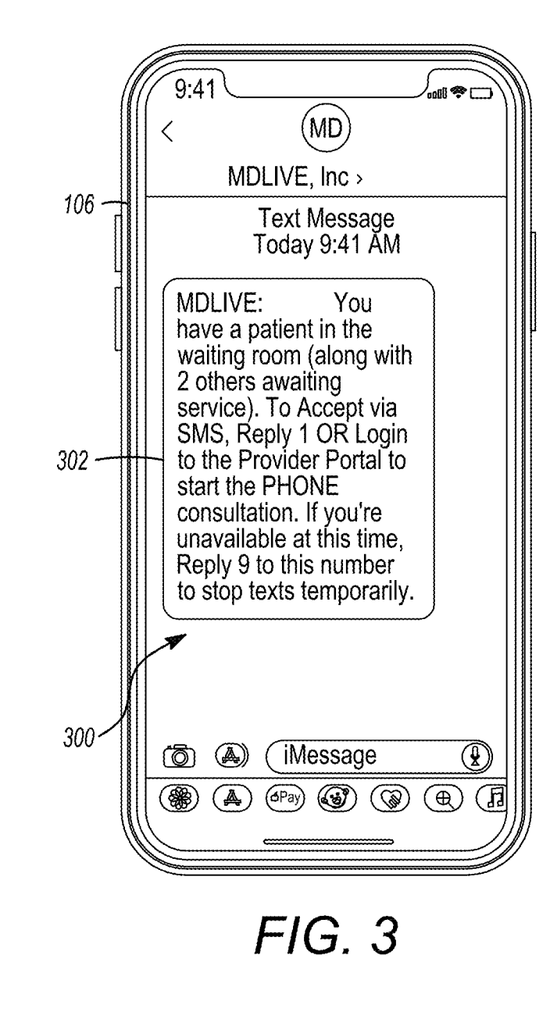
FIG. 3 illustrates another example of a GUI that can be displayed on a provider computing device shown in FIG. 1 to communicate notification and reply messages to the telehealth control system of the telehealth system.

The GUI 300 shown in FIG. 3 represents a notification message 302 sent from the control system 102 to the provider computing device 106 via the second channel 122. This notification message 302 informs the provider that more than one patient is waiting in the virtual waiting room for a teleconference with the provider and invites the provider to use his or her provider computing device 106 to send a reply message to accept the invitation to meet with the patient via the first channel 120. The notification message 302 also provides the provider with the option to send a reply message via the second channel 122 to decline the invitation to meet with any of the patients via the first channel 120 and to stop the control system 102 from sending additional notification messages via the second channel 122 for a temporary time period.

Figure 4:
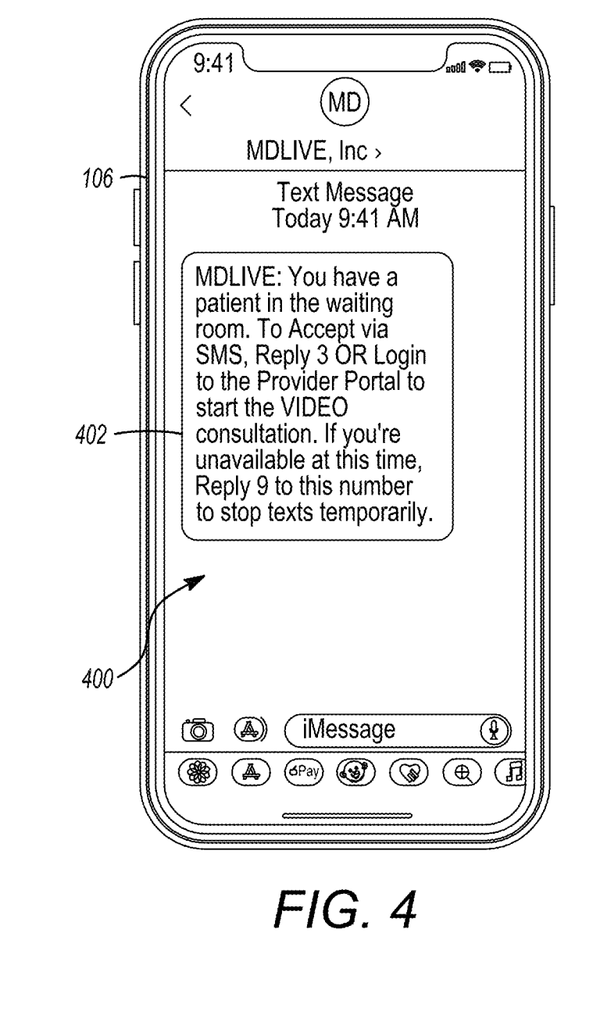
FIG. 4 illustrates another example of a GUI that can be displayed on a provider computing device shown in FIG. 1 to communicate notification and reply messages to the telehealth control system of the telehealth system.

The GUI 400 shown in FIG. 4 represents a notification message 402 sent from the control system 102 to the provider computing device 106 via the second channel 122. This notification message 402 informs the provider that a single patient is waiting in the virtual waiting room for a videoconference and invites the provider to use his or her provider computing device 106 to send a reply message to accept the invitation to meet with the patient via the first channel 120. The notification message 402 also provides the provider with the option to send a reply message via the second channel 122 to decline the invitation to meet with the patient via the first channel 120 and to stop the control system 102 from sending additional notification messages via the second channel 122 for a temporary time period.

Figure 5:
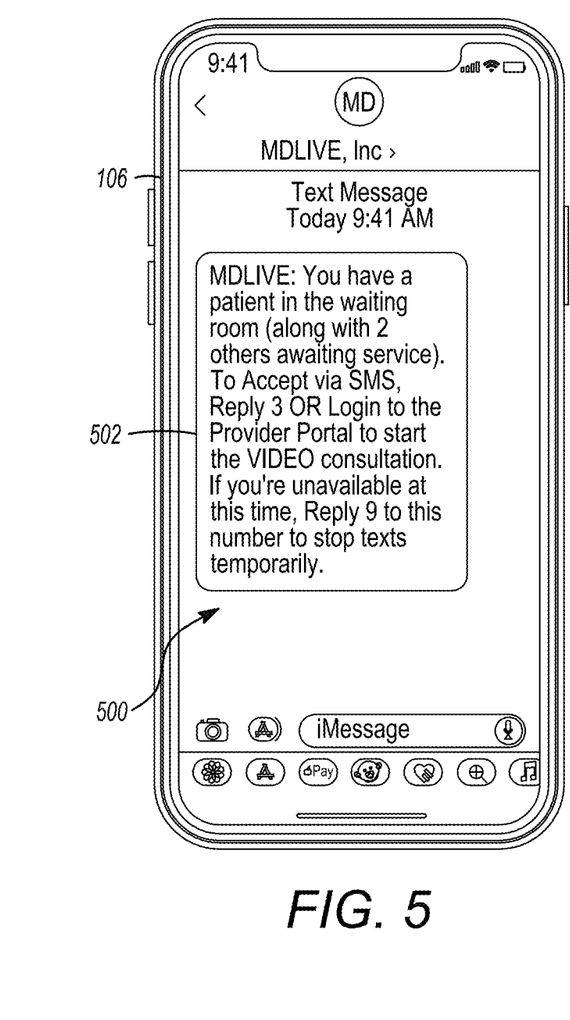
FIG. 5 illustrates another example of a GUI that can be displayed on a provider computing device shown in FIG. 1 to communicate notification and reply messages to the telehealth control system of the telehealth system.

The GUI 500 shown in FIG. 5 represents a notification message 502 sent from the control system 102 to the provider computing device 106 via the second channel 122. This notification message 502 informs the provider that more than one patient is waiting in the virtual waiting room for a videoconference with the provider and invites the provider to use his or her provider computing device 106 to send a reply message to accept the invitation to meet with the patient via the first channel 120. The notification message 502 also provides the provider with the option to send a reply message via the second channel 122 to decline the invitation to meet with any of the patients via the first channel 120 and to stop the control system 102 from sending additional notification messages via the second channel 122 for a temporary time period.

Figure 6:
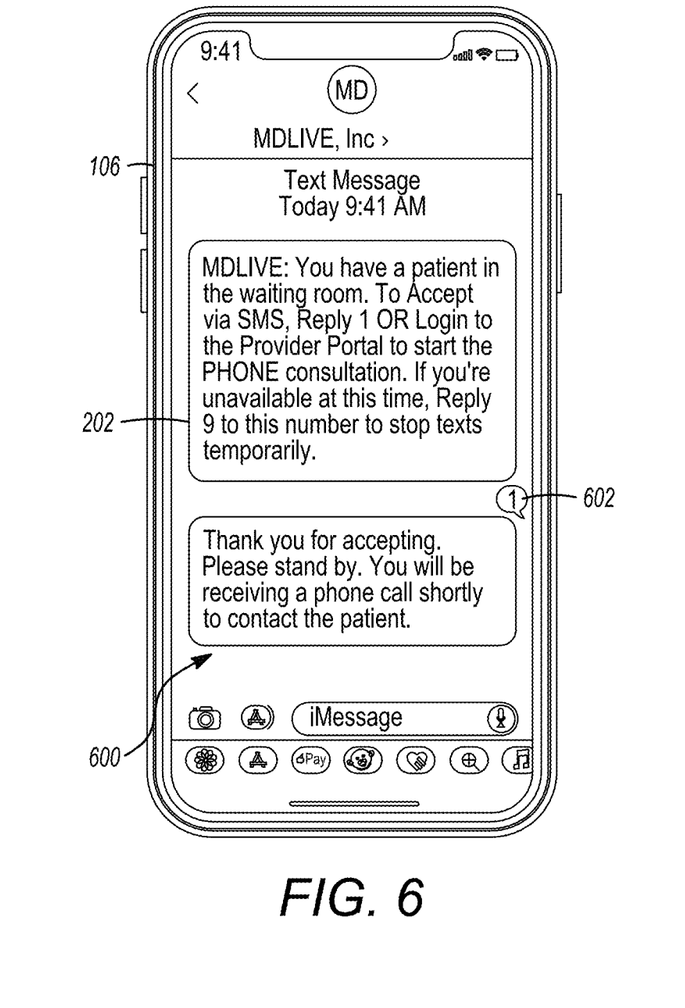
FIG. 6 illustrates another example of a GUI that can be displayed on a provider computing device shown in FIG. 1 to communicate notification and reply messages to the telehealth control system of the telehealth system.

The GUI 600 shown in FIG. 6 represents a reply message 602 sent from the provider computing device 106 to the control system 102 via the second channel 122. This reply message 602 informs the control system 102 that the provider has accepted the invitation to meet with the patient via a teleconference. The control system 102 may begin the teleconference via the first channel 120 by initiating a telephone call between the patient computing device 110 and the provider computing device 106.

Figure 7:
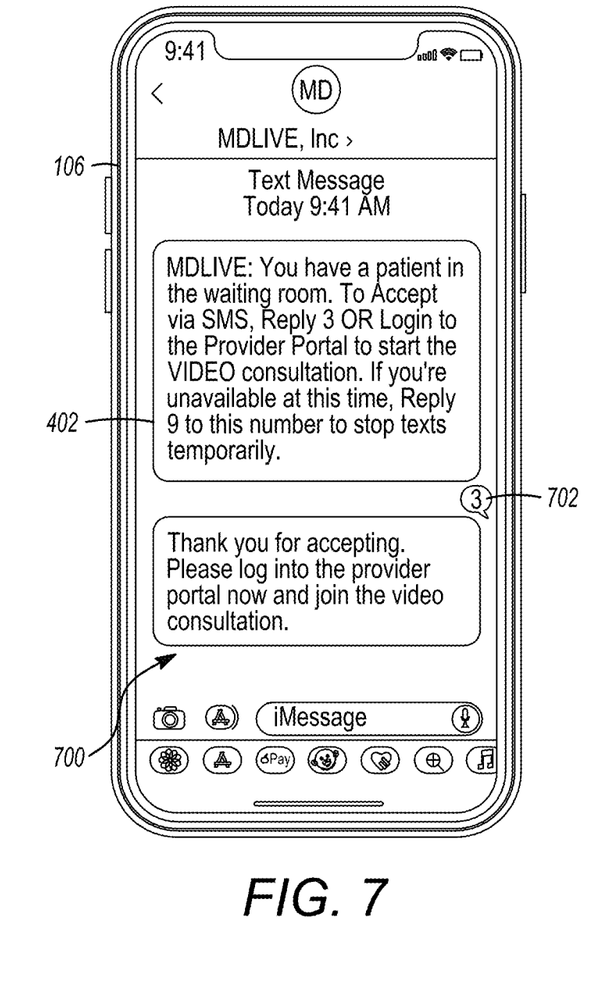
FIG. 7 illustrates another example of a GUI that can be displayed on a provider computing device shown in FIG. 1 to communicate notification and reply messages to the telehealth control system of the telehealth system.

The GUI 700 shown in FIG. 7 represents a reply message 702 sent from the provider computing device 106 to the control system 102 via the second channel 122. This reply message 702 informs the control system 102 that the provider has accepted the invitation to meet with the patient via a teleconference. The control system 102 may send an instructional message 704 in response that directs the provider to initiate the application 116 or access the website 118 on the provider computing message 106 to meet with the patient via the first channel 120.

Figure 8:
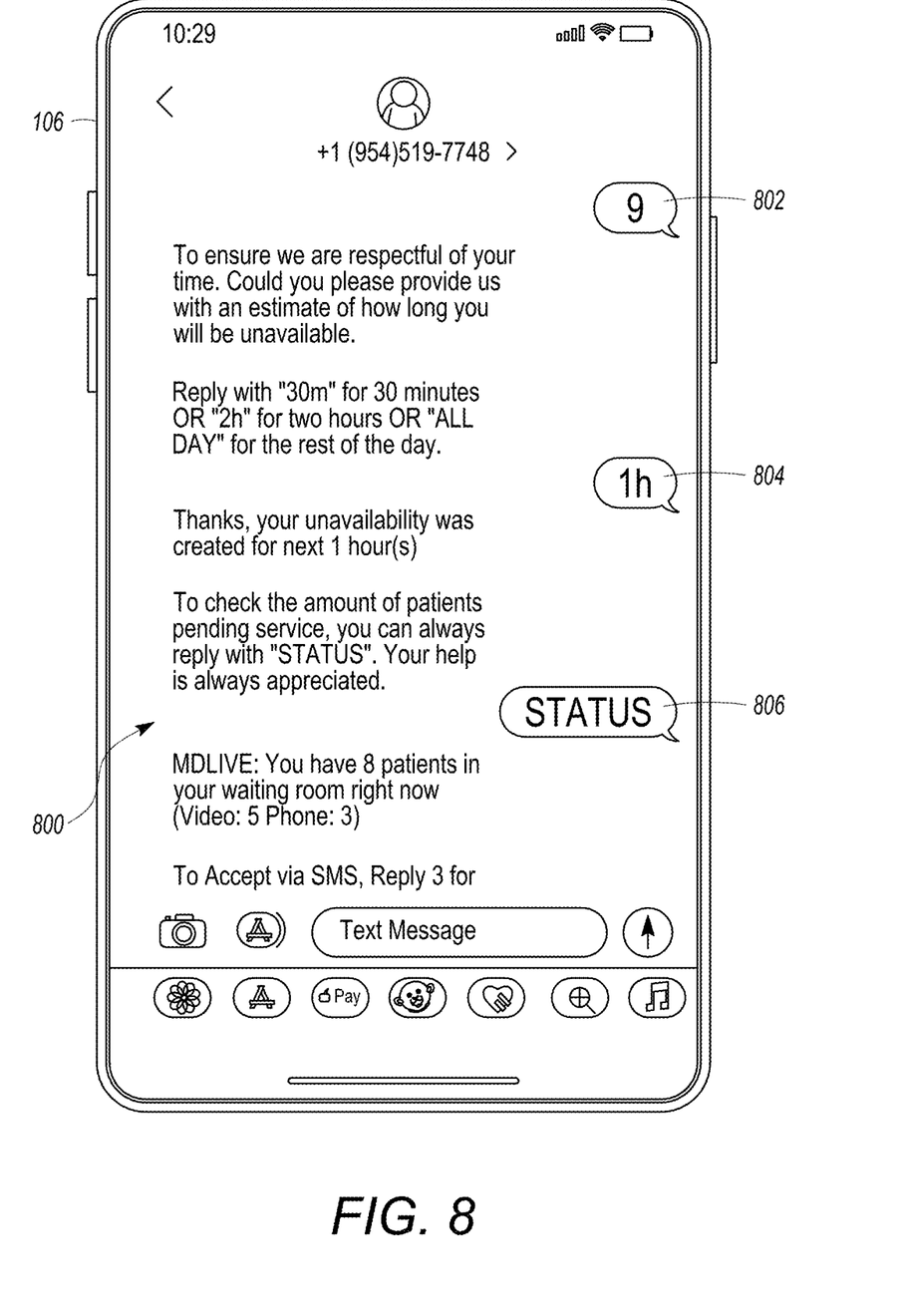
FIG. 8 illustrates another example of a GUI that can be displayed on a provider computing device shown in FIG. 1 to communicate notification and reply messages to the telehealth control system of the telehealth system.

The GUI 800 shown in FIG. 8 represents a reply message 802 sent from the provider computing device 106 to the control system 102 via the second channel 122. This reply message 802 notifies the control system 102 that the provider does not want to meet with any patients via the first channel 120 at this time. Optionally, the provider can use the provider computing device 106 to send one or more additional reply messages 804, 806 to the control system 102 via the second channel 122. The reply message 804 can notify the control system 102 that the provider does not want to receive any additional notification messages for a designated period of time, such as one hour. The reply message 806 can request the control system 102 notify the provider of how many patients are waiting in the virtual waiting room for a virtual encounter with one or more providers.

In various embodiments, the control system 102 generates a message that includes various dedicates at least one and maybe two or more action triggers embedded therein. The triggers can be an alphanumeric character that when received back from the provider device 106 at the control system 102 launches an action at the control system, e.g., over another communication channel, e.g., the first communication channel between the provider device and patient device. The provider electronic device 106 can send one or more actions triggers back to the control system 102 over the second communication channel 122.

In various embodiments, the control system 102 may send notification messages via the second channel 122 that inform providers of incentives to initiate one or more virtual encounters via the first channel 120. As one example, these incentives may be financial in nature, such as extra payment for taking an appointment. Certain time periods (e.g., between 9 p.m. and 8 a.m.) and/or days (e.g., weekends and holidays) may have far fewer providers available for virtual encounters. The control system 102 may offer increased pay to providers to conduct virtual encounters during these time periods or days relative to other time periods or days to increase the number of providers that are available to provide care or other services to patients via the first channel 120.

Figure 9:
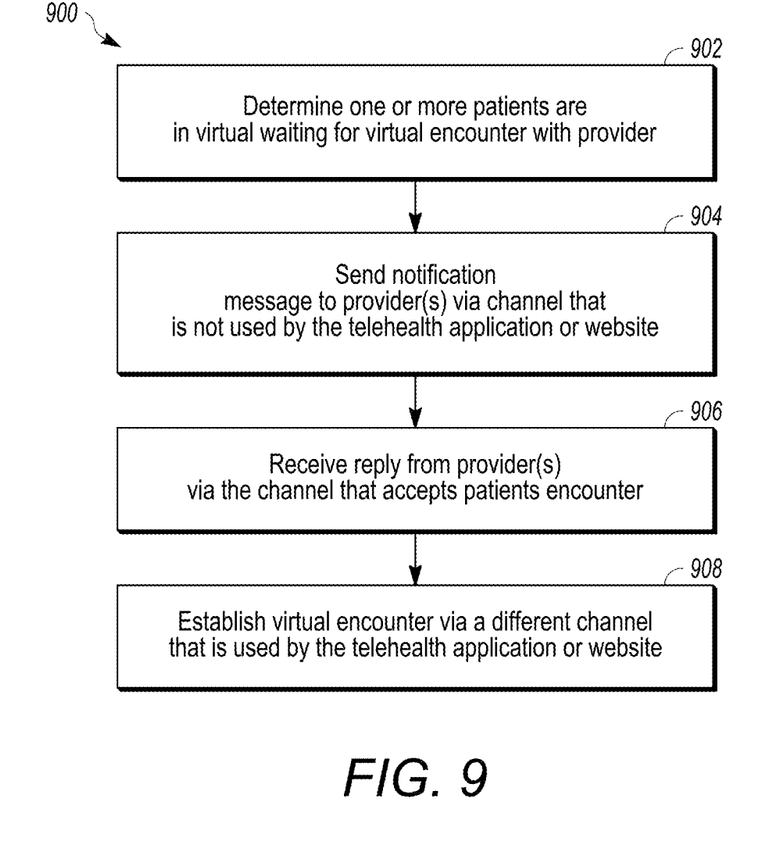
FIG. 9 illustrates a flowchart of one example of a method for engaging providers to participate in virtual encounters with patients in a telehealth system.

FIG. 9 illustrates a flowchart of one example of a method 900 for engaging providers to participate in virtual encounters with patients in a telehealth system. The method 900 can represent operations performed by the control system 102 shown in FIG. 1. At 902, a determination is made that one or more patients are waiting for a virtual encounter in a virtual waiting room. The control system 102 can receive requests from patient computing devices 108, 110 for virtual appointments with providers. Until the requests are met by starting a virtual appointment, the patients may wait for an appointment in the virtual waiting room.

At 904, one or more notification messages are sent to computing devices of the providers. The notification messages are sent to inform the providers of the patient(s) waiting for a virtual encounter with the providers. The notification messages may be sent only to those providers having expertise, education, certification, or training in the areas or issues about which the patients wish to virtually meet with the providers. The notification messages are sent via a communication channel that is not used by the telehealth software application or website through which the virtual encounters occur. For example, the notification messages may be sent via SMS text, MMS messages, or the like.

At 906, a reply message is received from one or more providers. This message may indicate acceptance of a patient for a virtual encounter. The reply message may accept the next patient in the queue, or the patient that has been waiting the longest for a virtual appointment. This can help ensure that the providers do not select patients for other reasons, such as by "cherry picking" or selecting patients having less complicated issues for the virtual encounters before patients having more complex issues.

At 908, a virtual encounter is established between the provider computing device and the patient computing device via a channel that is different from the channel used to send the notification message. For example, the control system can open a videoconference or teleconference via the telehealth system software application or website. The virtual encounter between the provider and patient can occur via this other channel.

Figure 10:
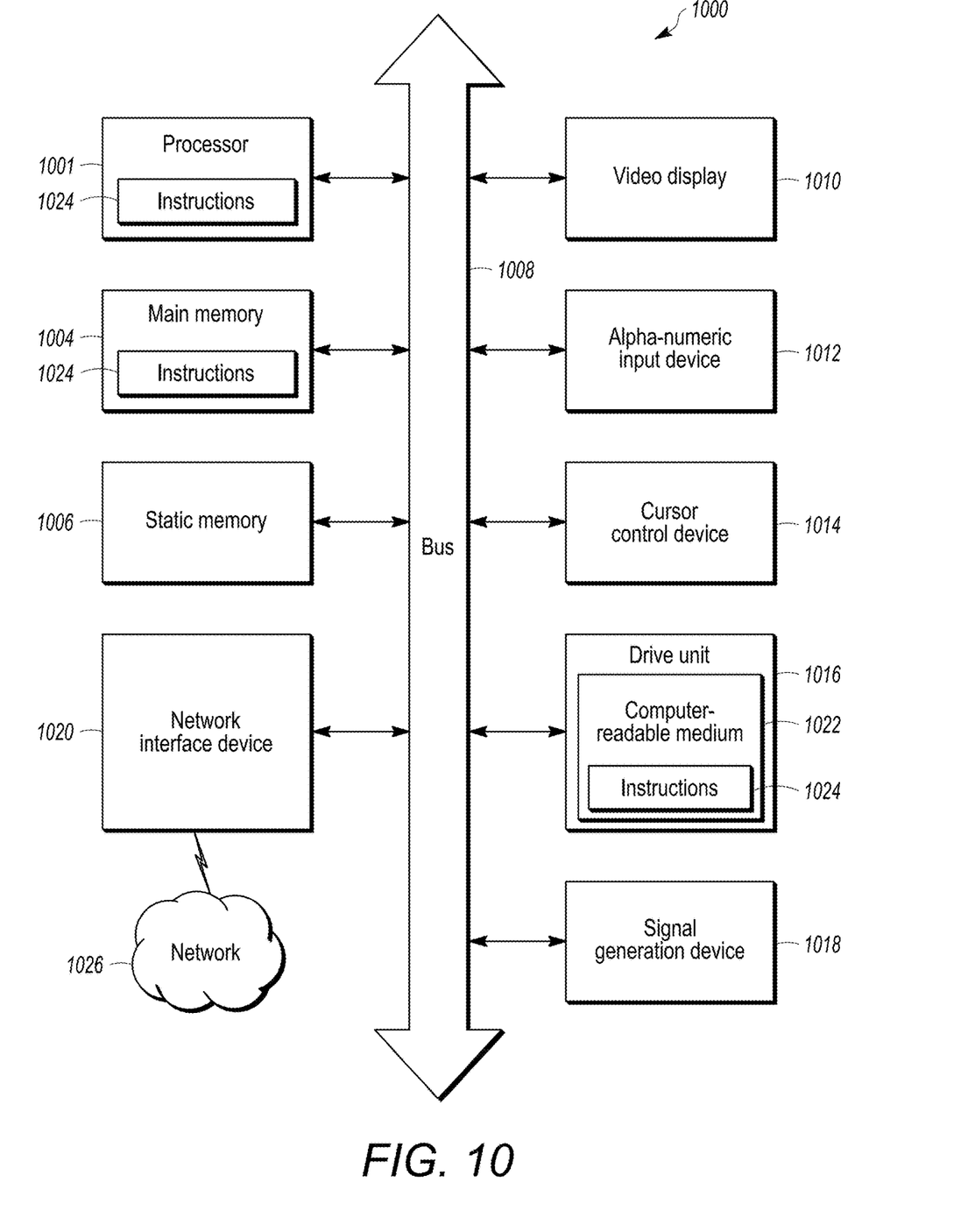
FIG. 10 shows a block diagram of a computer system within which a set of instructions may be executed causing the machine to perform any one or more than one methods, processes, operations, or methodologies discussed herein.

FIG. 10 shows a block diagram of a computer system 1000 within which a set of instructions may be executed causing the machine to perform any one or more than one methods, processes, operations, or methodologies discussed herein. For example, the system 1000 may represent the control system 102 shown in FIG. 1. The devices 1006-1030, for example, may include the functionality of the computer system 1000. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 1000 includes a processor 1002 (e.g., a central processing unit (CPU), a graphics processing unit (GPU) or both, etc.), a main memory 1004 and a static memory 1006, which communicate with each other via a bus 1008. The computer system 1000 further includes a video display unit 1010 (e.g., a liquid crystal display (LCD) or a cathode ray tube (CRT), etc.). The computer system 1000 also includes an alphanumeric input device 1012 (e.g., a keyboard, etc.), a cursor control device 1014 (e.g., a mouse, etc.), a drive unit 1016, a signal generation device 1018 (e.g., a speaker, etc.) and a network interface device 1020.

The drive unit 1016 includes a computer readable medium 1022 on which is stored one or more than one sets of instructions 1024 (e.g., software, etc.) embodying any one or more than one methodologies or functions described herein. The instructions 1024 may also reside, completely or at least partially, within the main memory 1004 and/or within the processor 1002 during execution thereof by the computer system 1000, the main memory 1004 and the processor 1002 also constituting non-transitory computer readable media. When loaded with the instructions 1024, the processor 1002 is a machine dedicated to only the present processes and methodologies.

The instructions 1024 may further be transmitted or received over a network 1026 via the network interface device 1020. The instructions can implement multiple communication channels to a provider, e.g., to multiple provider devices and the telehealth control system with one channel being a patient channel that provides data related to the patient and providing connection directly to the patient and a second channel that is a packet channel to provide text messages (e.g., non-video or non-audio communication). The network 1026 can represent the network(s) 112 shown in FIG. 1. While the computer-readable medium 1022 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that is capable of storing or encoding a set of instructions for execution by the machine and that cause the machine to perform any one or more than one methodologies of the present disclosure. The term "computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

Figure 11:
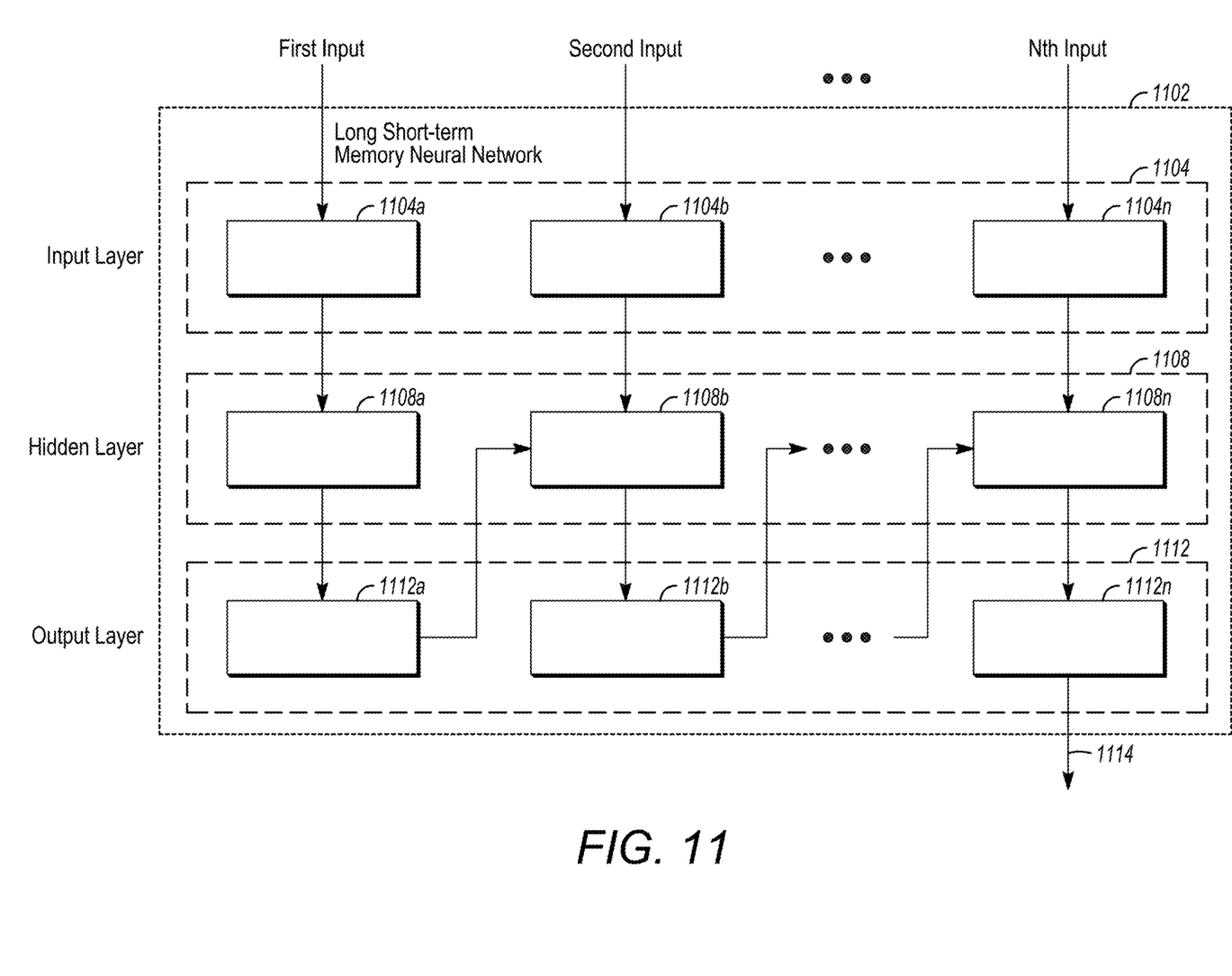
FIG. 11 illustrates a functional block diagram of an example artificial neural network that can be used by or represent one or more of the telehealth control systems described herein.

In at least one embodiment of the subject matter described herein, one or more decisions described above may be made using an artificial intelligence (AI) system or machine learning system. FIG. 11 illustrates a functional block diagram of an example artificial neural network 1102 that can be used by or represent one or more of the telehealth control systems described herein. In an example, the neural network 1102 can represent a long short-term memory (LSTM) neural network. In an example, the neural network 1102 can represent one or more recurrent neural networks (RNN). The neural network 1102 may be used to implement the machine learning as described herein, and various implementations may use other types of machine learning networks. The neural network 1102 includes an input layer 1104, one or more intermediate or hidden layers 1108, and an output layer 1112. Each layer 1104, 1108, 1112 includes artificial individual units, or neurons. The neurons may be mathematical functions that emulate models of biological neurons. The neurons may be artificial, elementary units in the artificial neural network 1102. Each neuron can receive information (e.g., as input into the neural network 1102 or as received as output from another neuron in another layer or the same layer), process this information to generate output, and provide the output to another neuron or as output of the neural network 1102. The input layer 1104 may include several input neurons 1104a, 1104b . . . 1104n, the hidden layer 1108 may include several intermediate neurons 1108a, 1108b . . . 1108n, and the output layer 1112 may include several output neurons outputs 1112a, 1112b . . . 1112n. The inputs may include, for example, a number of patients requesting a telehealth visit with a provider, the types of providers needed for the requested telehealth visits (e.g., based on expertise or training of the providers), communication channels that are available for communication, the day and/or time that a telehealth encounter is requested, or the like.

Each neuron can receive an input from another neuron and output a value to the corresponding output to another neuron (e.g., in the output layer 1312 or another layer). For example, the intermediate neuron 1308a can receive an input from the input neuron 1304a and output a value to the output neuron 1312a. Each neuron may receive an output of a previous neuron as an input. For example, the intermediate neuron 1308b may receive input from the input neuron 1304b and the output neuron 1312a. The outputs of the neurons may be fed forward to another neuron in the same or different intermediate layer 1308.

The processing performed by the neurons may vary based on the neuron, but can include the application of various rules or criteria described herein to partially or entirely decide which channel to use for sending a message to a provider, which providers to send messages to, which devices of the providers to send messages, the types of messages or signals to send to provider devices, etc. The output of the application of the rule or criteria can be passed to another neuron as input to that other neuron. One or more output neurons 1112n in the output layer 1112 may output a messaging decision 1114. This decision 1114 can be or represent a signal indicating the decision made by the neural network 1102, such as which channel to use to send a message, which providers to send the message to, which provider devices to send the message to, the type of message or signal to send, or the like. Although the input layer 1104, the intermediate layer(s) 1108, and the output layer 1112 are depicted as each including three artificial neurons, one or more of these layers may contain more or fewer artificial neurons. The neurons can include or apply one or more adjustable parameters, weights, rules, criteria, or the like, to perform the processing by that neuron.

In some embodiments, the neural network 1102 may be a convolutional neural network. The convolutional neural network can include an input layer, one or more hidden or intermediate layers, and an output layer. In a convolutional neural network, however, the output layer may include one fewer output neuron than the number of neurons in the intermediate layer(s), and each neuron may be connected to each output neuron. Additionally, each input neuron in the input layer may be connected to each neuron in the hidden or intermediate layer(s).

Such a neural network-based telehealth control system can be trained by operators, automatically self-trained, or can be trained both by operators and by the telehealth control system itself to improve how messages are sent, which channels are used, etc. This can allow for the telehealth control system to improve the speed in which patients are matched to providers for telehealth encounters to reduce delay and waiting times for patients waiting for telehealth encounters.

The machine-learning model used by the neural network 1102 can be or include a mathematical representation of relationships between different channels, different provider devices, different types of messages, different types of messages, etc., as generated using the machine-learning processes described herein. For example, the model may dictate that a first request received on a first day and/or first time and/or requesting a first type of provider (e.g., first type of provider expertise) is to be communicated to a first set or subset of fewer than all providers, is to be sent via a first channel, and/or is to be sent to a first type of provider devices (e.g., cell or mobile phones), while the same model may dictate that a second request received on a different day and/or different time, and/or requesting a different type of provider is to be communicated to a different set of providers, is to be sent via a different channel, and/or is to be sent to a different type of provider devices (e.g., laptop or desktop computer).

Input (e.g., the date and/or time a request is received, the number of patients requesting a telehealth encounter, the available communication channels, and/or the different areas of expertise of providers) may be provided to one or more of the input neurons of the neural network 1102 after the model is created. The input may be communicated or otherwise provided by operator input, by one or more of the patient and/or provider devices 104, 106, 108, 110, or the like. The output neurons within the network 1102 generate an output based on the relationships that are derived or learned by the neurons in the intermediate or hidden layer(s) 1108. Connections between the nodes within each layer and/or between the layers 1104, 1108, 1112 and/or the neurons may be created via the process of training the neural network 1102. This training can adjust connections, values of parameters, weights, rules, etc., in the models used to determine which channel to use, which providers to send messages to, which provider devices to send messages to, and which channel to send messages. This repeated training process can be referred to as deep learning.

This training can involve, for example, providing input to the neurons in the input layer 1104 of the telehealth control system, and having the neurons in the input layer 1104 and/or intermediate layer(s) 1108 of the record matching system apply the rules, criteria, and/or processes that associate different inputs or set of inputs with different decisions (e.g., which channel to use, which providers to send the message to, which provider devices to send the message, the type of message to send, etc.). This output 1114 can then be examined to determine whether the output is correct or not. For example, patient wait times associated with different outputs 1114 from the neural network 1102 can be examined over time to determine whether the model(s) can be changed and reduce the wait times. This analysis and decision can be performed by one or more of the neurons in the layers 1104, 1108, 1112 of the neural network 1102, or can be manually performed (e.g., as a check on operation of the neural network 1102). This process can be repeated several times to reduce the wait times experienced by patients in finding providers for participating in telehealth encounters.

The present disclosure uses the term "message" and the like for describing communication over a secondary communication channel to and from the provider devices. In an example embodiment, the message is not an audio signal. In an example embodiment, the message is not a video signal. Messages can be secure (e.g., encoded, encrypted, or the like) electronic packetized communication. Messages can be SMS text messages in an example embodiment. Messages can be text messages in an example embodiment. The messages can be packets including a header (including sender device and recipient device identification data) and a body of data. The use of a packet for communication on the second channel can allow for the packet to require less bandwidth to route the information to and from the provider device. Routing the packets can use internet protocol (e.g., IPv4, IPv6 and the like) to transmit the packets. The packet replies from the provider device can be a selection reply, e.g., a single character, that in and of itself does not provide any protected or sensitive information and can be interpreted by the telehealth system.

The use of the first communication channel and the second communication channel can provide for more efficient connection between provider devices and patient devices, as well as computers and communication channels. The first channel can be a private, encrypted channel, which may include protected, private data, which can be through the telehealth system connecting the patient device and the selected provider device. The first channel can provide for menus or selectable information. In an example, the first channel can include patient health information. The second channel is a communication between the telehealth system and provider device, which may not be the same device on which a provider can provide the telehealth consultation with the patient. The second channel can be point to point communication channel over a public communication system and may include data that does not include any protected, private data. In an example embodiment, the second channel does not include patient identifying information or patient health information. The initial message over the second channel can provide instructions for how to reply to indicate a specific action that is to occur over the first channel. The reply message can include the indication of the specific action, e.g., using a single digit or single character.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims is intended to be a means-plus-function element within the meaning of 35 U.S.C. § 112(f) unless an element is expressly recited using the phrase "means for," or in the case of a method claim using the phrases "operation for" or "step for."

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, present disclosure may lie in less than all features of a single disclosed embodiment. Thus, the following claims are hereby incorporated into the Detailed Description, with each claim standing on its own as a separate embodiment.

What is claimed is:

1. A method for engaging healthcare providers with patients in virtual encounters, the method comprising:
   determining that one or more of the patients are waiting for the virtual encounters with the healthcare providers via a telehealth system software application operating on computing devices of the healthcare providers or via a telehealth system website accessible via the computing devices of the healthcare providers;
   sending a notification message to the computing device of one or more of the healthcare providers via a first communication channel that is outside of the telehealth system software application and the telehealth system website;
   receiving a reply message from the computing device of the one or more of the healthcare providers via the first communication channel, the reply message indicating acceptance of at least one of the virtual encounters by the one or more of the healthcare providers; and
   establishing the at least one of the virtual encounters between the one or more of the healthcare providers and the one or more of the patients via a second communication channel that is different from the first communication channel.

2. The method of claim 1, further comprising selecting one or more of the first communication channel from among two or more different communication channels using an artificial neural network.

3. The method of claim 1, wherein the notification message that is sent via the first communication channel is a short messaging service text message.

4. The method of claim 1, wherein the reply message that is received via the first communication channel is a short messaging service text message.

5. The method of claim 1, wherein the notification message is sent to a mobile phone of the one or more of the healthcare providers and the reply message is received from the mobile phone of the one or more of the healthcare providers.

6. The method of claim 1, wherein the notification message is sent, and the reply message is received via the first communication channel that does not extend between the computing device of the one or more of the healthcare providers and a computing device of the patients that are used to conduct the at least one of the virtual encounters.

7. The method of claim 1, wherein the at least one of the virtual encounters is established via the second communication channel that includes or extends between the telehealth system software application operating on the computing devices of the healthcare providers or the telehealth system website accessible via the computing devices of the healthcare providers.

8. The method of claim 1, wherein the notification message is sent, and the reply message is received via the first communication channel that extends between or through cellular towers and the at least one of the virtual encounters is established outside of the cellular towers.

9. A telehealth control system for engaging healthcare providers with patients in virtual encounters, the telehealth control system comprising:
one or more processors configured to determine that one or more of the patients are waiting for the virtual encounters with the healthcare providers via a telehealth system software application operating on computing devices of the healthcare providers or via a telehealth system website accessible via the computing devices of the healthcare providers, the one or more processors configured to send a notification message to the computing device of one or more of the healthcare providers via a first communication channel that is outside of the telehealth system software application and the telehealth system website, the one or more processors configured to receive a reply message from the computing device of the one or more of the healthcare providers via the first communication channel, the reply message indicating acceptance of at least one of the virtual encounters by the one or more of the healthcare providers, and the one or more processors are configured to establish the at least one of the virtual encounters between the one or more of the healthcare providers and the one or more of the patients via a second communication channel that is different from the first communication channel.

10. The telehealth control system of claim 9, wherein the one or more processors are configured to send the notification message as a short messaging service text message.

11. The telehealth control system of claim 9, wherein the one or more processors are configured to receive the reply message as a short messaging service text message.

12. The telehealth control system of claim 9, wherein the one or more processors are configured to send the notification message to a mobile phone of the one or more of the healthcare providers and to receive the reply message from the mobile phone of the one or more of the healthcare providers.

13. The telehealth control system of claim 9, wherein the one or more processors are configured to establish the at least one of the virtual encounters as a videoconference or a teleconference via the Internet.

14. The telehealth control system of claim 9, wherein the one or more processors are configured to send the notification message and to receive the reply message via the first communication channel that does not extend between the computing device of the one or more of the healthcare providers and a computing device of the patients that are used to conduct the at least one of the virtual encounters.

15. The telehealth control system of claim 9, wherein the one or more processors are configured to establish the at least one of the virtual encounters via the second communication channel that includes or extends between the telehealth system software application operating on the computing devices of the healthcare providers or the telehealth system website accessible via the computing devices of the healthcare providers.

16. The telehealth control system of claim 9, wherein the one or more processors are configured to send the notification message and to receive the reply message via the first communication channel that extends between or through cellular towers and the one or more processors are configured to establish the at least one of the virtual encounters outside of the cellular towers.

17. A method for engaging service providers with consumers in virtual encounters, the method comprising:
determining that one or more of the consumers are waiting for the virtual encounters with the service providers via a software application operating on computing devices of the service providers or via a system website accessible via the computing devices of the service providers;
sending a notification message to the computing device of one or more of the service providers via a first communication channel that is outside of the software application and the system website;
receiving a reply message from the computing device of the one or more of the service providers via the first communication channel, the reply message indicating acceptance of at least one of the virtual encounters by the one or more of the service providers; and
establishing the at least one of the virtual encounters between the one or more of the service providers and the one or more of the consumers via a second communication channel that is different from the first communication channel.

18. The method of claim 17, further comprising selecting a type of the notification message to send using an artificial neural network.

19. The method of claim 17, wherein the notification message that is sent via the first communication channel is a short messaging service text message.

20. The method of claim 17, wherein the notification message is sent to a mobile phone of the one or more of the service providers and the reply message is received from the mobile phone of the one or more of the service providers.

* * * * *